United States Patent [19]

Mattner et al.

[11] Patent Number: 4,530,796

[45] Date of Patent: Jul. 23, 1985

[54] PROCESS FOR THE PREPARATION OF ISOCYANATES THROUGH THE THERMAL CLEAVAGE OF URETHANES

[75] Inventors: Otto Mattner, Speyer; Franz Merger, Frankenthal; Friedrich Towae, Ludwigshafen, all of Fed. Rep. of Germany

[73] Assignee: BASF Aktiengesellschaft, Ludwigshafen, Fed. Rep. of Germany

[21] Appl. No.: 664,782

[22] Filed: Oct. 25, 1984

[30] Foreign Application Priority Data

Oct. 29, 1983 [DE] Fed. Rep. of Germany ....... 3339300

[51] Int. Cl.³ .............................................. C07C 69/00
[52] U.S. Cl. ................................................. 260/453 P
[58] Field of Search ..................................... 260/453 P

[56] References Cited

U.S. PATENT DOCUMENTS

| | | | |
|---|---|---|---|
| 4,003,938 | 1/1977 | Koenig et al. | 260/453 |
| 4,069,238 | 1/1978 | Zanker | 260/453 |
| 4,081,472 | 3/1978 | Tsumura et al. | 260/453 |
| 4,195,031 | 3/1980 | Reichmann et al. | 260/453 |

*Primary Examiner*—Alan Siegel
*Attorney, Agent, or Firm*—William G. Conger; Joseph D. Michaels

[57] ABSTRACT

A process for the pyrolysis of mono-, di-, and polyurethanes to the corresponding mono-, di-, and polyisocyanates wherein the urethane to be cleaved is heated under pressure and sprayed through a nozzle into a pyrolysis chamber maintained at reduced pressure. The isocyanate and alcohol cleavage products are separated by fractional condensation.

20 Claims, No Drawings

PROCESS FOR THE PREPARATION OF ISOCYANATES THROUGH THE THERMAL CLEAVAGE OF URETHANES

BACKGROUND OF THE INVENTION

1. Field of the Invention

The present invention relates to a process for the pyrolysis of urethanes to the corresponding isocyanates. The process allows the production of mono-, di-, and polyisocyanates while eliminating problems associated with prior processes.

2. Description of the Prior Art

The industrial production of organic mono- and polyisocyanates is generally performed by the phosgenation of the corresponding organic amines to carbamic acid chlorides followed by pyrolysis. This process, however, is subject to well known disadvantages with respect to environmental protection and safety due to the toxic nature of both starting materials and process by-products.

Isocyanates may also be produced by subjecting to pyrolysis N-substituted urethanes either in the gaseous or in the liquid phase. However, various additional undesired side reactions frequently take place during such thermal cleavage. Typical examples of these side reactions are decarboxylation of the urethanes, which may be accompanied by the formation of primary and secondary amines as well as olefins; the reaction between the isocyanate and urethane which produce allophanates and amine which in turn may react to form ureas; and the polymerization of the isocyanates to form crystalline isocyanurates.

According to German patent document No. 19 44 719 (British Patent No. 1,247,451), for example, urethanes are pyrolyzed at temperatures from 400° to 600° C. in the presence of Lewis acid catalysts. The isocyanate and the alcohol produced by the pyrolysis are separated by means of fractional condensation. By this process, for example, 2,4-toluene diisocyanate may be obtained through the pyrolysis of toluene-2,4-diethylurethane in the presence of iron(III) fluoride. Some of the disadvantages of this reaction are low yields, significant amounts of polymeric by-product, decomposition of the catalyst, and corrosion of the reaction equipment.

In U.S. Pat. No. 3,870,739 a process is described in which an aromatic urethane is subjected to pyrolysis at a temperature from 350° to 550° C. and a pressure less than (m+1) times the isocyanate vapor pressure wherein m is the number of urethane groups in the aromatic urethanes. The pyrolysis occurs in a catalyst-free pyrolysis zone wherein the residence time of the pyrolysis products is less than 15 seconds. One of the disadvantages of this process is that a solid polymer is produced as a by-product. This solid polymeric by-product clogs the pyrolysis reactor and associated equipment necessitating both extensive separation problems as well as frequent process down time. These problems make a continuous process difficult to operate.

Thermal cleavage of urethanes in the liquid phase is described in U.S. Pat. No. 3,962,302 and U.S. Pat. No. 3,912,280. In the former, the urethanes are dissolved in an inert solvent such as alkylbenzenes, aliphatic and cycloaliphatic hydrocarbons, or phthalate esters and are cleaved under normal or superatmospheric pyrolysis reactor pressure at temperatures of from 175° to 350° C. The isolation and separation of the resulting isocyanate and alcohol are achieved either by using the solvent or an inert gas as a carrier. In U.S. Pat. No. 3,912,280, high molecular weight substituted or unsubstituted aliphatic, cycloaliphatic, or aromatic hydrocarbons, ethers, esters, or ketones are used as the solvent. Separation of the cleavage products is achieved by distillation. Isocyanate, alcohol, and inert gas carrier are taken off as the overhead, while the solvent is taken off as the bottom fraction.

In order to produce aromatic isocyanates by the process of U.S. Pat. No. 4,081,472, urethanes are pyrolyzed at temperatures of 150° to 350° C. under reduced pressure through contact with a solution containing at least 0.001 weight percent of at least one metal ion, such as ions of copper, zinc, aluminum, tin, titanium, vanadium, iron, cobalt, and nickel as catalyst, dissolved in a solvent having a boiling point of 200° C. The separation of the resulting cleavage products is achieved by means of fractional condensation. Here, however, polymerization products which cannot be distilled off remain in the solvent fraction which means that additional purification operations are required for the solvent containing the catalytically active metal ions.

In U.S. Pat. No. 4,330,479 pyrolysis is achieved by utilizing catalytically active, large-surface area metals present in a heterogenous phase. The disadvantage of this process is that the metals used as catalysts gradually lose their catalytic activity over time as a result of reduced surface availability caused by surface coating which consists of polymeric reaction by-products. Removal of these by-products also necessitates additional purification operations.

In order to eliminate this problem, European patent document No. 35 519 performs thermal cleavage in the presence of carbon, preferably as a solids charge in a fluidized bed. The advantage here is that the catalyst, deactivated by the polymeric by-products or decomposition products, does not need to be regenerated, but rather can be destroyed in a residue-free and environmentally sound manner by means of incineration. However, certain technical expenses are unavoidably linked to the sophisticated fluidized bed technology and to the regeneration procedures required for the fluidized packing.

SUMMARY OF THE INVENTION

Thus, in spite of the long-felt need for an efficient, economical process for the pyrolytic production of isocyanates, and in spite of the research efforts expended in this area, the known processes for producing isocyanates by means of thermal cleavage of carbamic acid chlorides or N-substituted urethanes, all possess well known disadvantages.

Accordingly, it is an object of the subject invention to provide a process for the thermal cleavage of urethanes to form the corresponding isocyanates, whereby said process would eliminate or at least reduce the problems associated with prior processes. It is a further object of the subject invention to provide a process capable of economically feasible continuous operation.

It was unexpectedly found that urethanes can be easily subjected to thermal cleavage in high yield when they are heated in the liquid phase under pressure, optionally in the presence of one or more solvents, and sprayed through a nozzle into a packed, evacuated pyrolysis reactor operating at elevated pressure.

The subject of the invention is, therefore, a process for the preparation of isocyanates through the thermal cleavage of urethanes in the gaseous phase at temperatures from 175° to 600° C., wherein the urethanes are heated in a liquid phase under pressure, sprayed into a pyrolysis reactor which is charged with a temperature-resistant, inert packing, through a nozzle which operates at elevated pressure, thereby cleaving the urethanes without the use of a catalyst.

Compared with previously known methods, the process of this invention produces isocyanates with very good yields using a method which is quite simple from an industrial standpoint, since no catalysts and, in some cases, no solvents are required which need to be regenerated or discharged. Furthermore, no upstream equipment is needed for urethane vaporization, equipment which otherwise would require cleaning after a period of time due to unavoidable decomposition reactions. The upstream urethane vaporization unit is not required since the urethanes, which have been preheated in the liquid phase under pressure, spontaneously cleave into isocyanate and alcohol when sprayed into the evacuated pyrolysis reactor following which the cleavage products are rapidly drawn out of the pyrolysis reactor.

DESCRIPTION OF THE PREFERRED EMBODIMENTS

The urethanes can be cleaved in the absence of solvents. In a preferred embodiment, however, the urethanes are mixed with inert solvents, in amounts from 5 to 50 parts by weight, preferably from 10 to 30 parts by weight per 100 parts by weight of urethane.

The urethanes, optionally in the presence of the inert solvent, are heated to temperatures from 100° to 400° C., preferably 130° to 350° C., at a pressure of from 20 to 300 bar, preferably from 50 to 200 bar, and sprayed into the pyrolysis reactor through a jet nozzle whose spray pressure is from 20 to 300 bar, preferably from 50 to 200 bar. The reactor charge is from 10 to 1000, preferably 100 to 500 urethane equivalents per liter reactor volume per hour.

When the urethane cleavage is performed in the presence of inert solvents, it is preferable to use those solvents whose boiling point lies between that of the resulting isocyanates and alcohol. Typical examples of solvents are: aliphatic hydrocarbons, such as the higher alkanes, e.g., decane, undecane, dodecane, tridecane, tetradecane, pentadecane, hexadecane, heptadecane, tetralin, decalin, and liquid paraffin; alicyclic hydrocarbons, such as petroleum fractions of the naphthene series; substituted or unsubstituted aromatic hydrocarbons such as naphthalene, 1- and 2-methylnaphthalene, 1,2-, 1,4-, 1,6-, 2,7-, 2,6-, and 2,3-dimethylnaphthalene, 1-ethylnaphthalene, phenylnaphthalene, benzylnaphthalene, toluene, 1,2-, 1,3-, and 1,4-dimethylbenzene, 1,2,4- and 1,3,5-trimethylbenzene, 1,2,3,5- and 1,2,4,5-tetramethylbenzene, 1,3,5-triethylbenzene, hexyl-, heptyl-, octyl-, nonyl-, and decylbenzene, hexaethylbenzene, diphenyl, 4,4'-dimethyldiphenyl, dibenzyl, diphenylmethane, and 4,4'-dimethyldiphenylmethane; halogen-substituted aromatic hydrocarbons such as chlorobenzene, 1,2- and 1,4-dichlorobenzene, 1,2,3,4-, 1,2,3,5-, and 1,2,4,5-tetrachlorobenzene, pentachlorobenzene; ethers such as diethylene glycol dimethyl ether, diethylene glycol diethyl ether, diisoamyl ether, di-n-amyl ether, dibenzyl ether, diphenyl ether, α-methylnaphthyl ether, and β-ethylnaphthyl ether.

The following have proven themselves to be particularly effective and are therefore preferred: substituted and unsubstituted aromatic hydrocarbons such as benzene, toluene, 1,2-, 1,3-, and 1,4-dimethylbenzene, 1,2,4- and 1,3,5-trimethylbenzene, 1,2,3,5- and 1,2,4,5-tetramethylbenzene, 1,3,5-triethylbenzene, hexyl-, heptyl-, octyl-, nonyl-, and decylbenzene; ethers such as, for example, diethylene glycol dimethyl ether, diethylene glycol diethyl ether, diisoamyl ether, di-n-amyl ethers, and alkanes such as as cyclohexane, heptane, octane, nonane, decane, undecane, dodecane, tridecane, tetradecane, pentadecane, hexadecane, heptadecane, tetralin, decalin, or mixtures thereof.

Urethanes which have been thermally cleaved into isocyanate and alcohol in accordance with the process of the invention have the general formula below.

$R(NHCOOR')_n$

In the above formula, R is a heterocyclic, aliphatic, cycloaliphatic, aromatic-aliphatic, or aromatic radical having from 1 to 60 carbon atoms, preferably from 4 to 20 carbon atoms. R is preferably a substituted or unsubstituted aryl or alkyl radical. Suitable alkyl radicals may be linear, branched, or cyclic and, in some cases, further may contain interspersed hetero atoms such as sulfur, oxygen, or nitrogen. Suitable aryl radicals may contain multiple aromatic rings connected with alkyl groups as bridge elements.

R' is an optionally substituted aliphatic, aromatic, or aromatic-aliphatic radical having from 1 to 20 carbon atoms, preferably from 1 to 10 carbon atoms, or a cycloaliphatic radical having from 3 to 15 carbon atoms, preferably from 3 to 7 carbon atoms.

In the formula, n is a whole number from 1 to about 6, preferably from 1 to 3, and more preferably from 1 or 2.

When R is an aryl radical, as in the case of the aryl urethanes, the optionally substituted aryl radicals may be derived from aromatic monoamines such as aniline, ortho-, meta-, and para-substituted anilines such as hydroxy-, methoxy-, ethoxy-, propoxy-, isopropoxy-, N-butoxy-, isobutoxy-, sec-butoxy, and tert-butoxyanilines; benzoic acid alkyl esters substituted by an amino group in the m-and/or p-position, having from 1 to 4 carbon atoms in the alkyl radical; N-alkoxycarbonylaminobenzenes and toluenes substituted by amino groups in the m- and/or p-position, having from 1 to 4 carbon atoms in the alkyl radical; α- and β-naphthylamine; aromatic diamines such as 1,3- and 1,4-diaminobenzene; 1,3-diaminobenzenes substituted by nitro, methyl, ethyl, n-propyl, isopropyl, n-butyl, isobutyl, secbutyl, tert-butyl, methoxy, ethoxy, n-propoxy, isopropoxy, n-butoxy, isobutoxy, sec-butoxy, tert-butoxy or halogen, preferably fluorine and/or chlorine; 1,4-diaminobenzene, 1,5- and 1,8-diaminonaphthalene, 4,4'-diaminodiphenyl, 2,2'-, 2,4'-, and 4,4'-diaminodiphenylmethane substituted in the 2-position, and the corresponding isomers mixtures; and aromatic polyamines, such as 1,3,5-triaminobenzene, 2,4,6-triaminotoluene, and 1,3,5-triaminonaphthalene.

In addition, in the case of the substituted and unsubstituted alkylurethanes, the alkyl radicals may be derived from alphatic monoamines such as methylamine, ethylamine, propylamine, isopropylamine, n-butylamine, secbutylamine, tert-butylamine, isobutylamine, 2- and 3-methylbutylamine, neopentylamine, n-pentylamine, 2-methylpentylamine, sec-isoamylamine, n-hexylamine, 2-methylhexylamine, 2-ethylhexylamine, n-heptylamine, n-octylamine, n-nonylamine, n-decylamine, n-dodecylamine, 2-phenylpropylamine, benzylamine, cyclopentylamine, cyclohexylamine, tertbutylcyclohexylamine; aliphatic diamines such as ethylenediamine, 1,3- and 1,2-propylenediamine, 2,2-dimethyl-1,3-propylenediamine, 1,4-butylenediamine, 2-ethyl-1,4-butylenediamine, 1,5-pentamethylenediamine, 2-methyl-1,5-pentamethylenediamine, 1,6-hexamethylenediamine, 2,2,4-trimethyl-1,6-hexamethylenediamine, 1,8-octamethylenediamine, 1,10-decylenediamine, 1,12-dodecylenediamine and 1,4-hexahydroxylylenediamine, cycloaliphatic diamines such as 1,2-, 1,3-, and 1,4-cyclohexanediamine, 2,4- and 2,6-hexahydrotoluenediamine, as well as the corresponding isomer mixtures, aliphatic-cycloaliphatic diamines such as 4,4'-, 2,4'-, and 2,2'-diaminodicyclohexylmethane as well as the corresponding isomer mixtures, 2,2-bis(4-aminocyclohexyl)-propane, 3-aminomethyl-3,5,5-trimethylcyclohexylamine, and dicyclopentadienyl compounds of formula

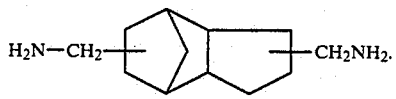

Also suitable are diamines containing in bonded form hetero atoms or heterocyclic radicals. Examples are 3,3'-diaminodipropylether, substituted and unsubstituted N,N'-bis(aminoalkyl)piperazine, e.g., N,N'-bis(2,2-dimethyl-3-aminopropyl)piperazine and N,N'-bis(aminopropyl)piperazine.

Typical examples of aryl urethanes which are thermally cleavable in the process of the invention are: N-phenyl methylurethane, N-phenyl ethylurethane, 3,5-dichlorophenyl ethylurethane, 4-methylphenyl ethylurethane, 2,4- and 2,6-toluene dimethylurethane, as well as the corresponding isomer mixtures, 2,4- and 2,6-toluene diethylurethane, 2,4- and 2,6-toluene dibutylurethane, 1,5-naphthalene diethylurethane, 4,4'-, 2,4'-, 2,2'-methylenediphenyl dimethylurethane, 4,4'-, 2,4'-, and 2,2'-methylenediphenyl dibutylurethane, 4,4'-, 2,4'-, and 2,2'-methylenediphenyl dihexylurethane, and the corresponding isomer mixtures.

Typical examples for alkyl urethanes are: N-methyl octylurethane, N-methyl hexylurethane, N-ethyl dodecylurethane, N-methyl phenylurethane, N-ethyl phenylurethane, N-propyl phenylurethane, N-propyl decylurethane, N-cyclohexyl methylurethane, 1,6-hexamethylene dibutylurethane, 1,6-hexamethylene diethylurethane, 1,6-hexamethylene dimethylurethane, 2,2,4-trimethyl-1,6-hexamethylene dibutylurethane, 1,4-hexahydroxylylene diethylurethane, 1,4-cyclohexyl dimethylurethane, 1,4-cyclohexyl dibutylurethane, and 3-(butoxycarbonylaminomethyl)-3,5,5-trimethylcyclohexyl butylurethane.

The cleavage of the previously heated urethanes occurs in the vapor phase when they are injected into the pyrolylsis zone provided by a pyrolysis reactor at temperatures of from 175° to 600° C., preferably from 300° to 480° C. and most preferably from 360° to 440° C. Injection may be either continuous or discontinuous into the pyrolysis reactor maintained at a reduced pressure generally equal to or less than 500 mbar, preferably from 0.1 to 200 mbar, and more preferably from 1 to 100 mbar.

The pyrolysis reactor, which generally has a column-like shape, may have any desired cross section, for example, rectangular, elliptical, or circular. Long, cylindrical pyrolysis reactors are preferred. Generally the ratio of the inside diameter to the length of the pyrolysis reactor is from 1:1 to 1:100, preferably from 1:10 to 1:500. The pyrolysis reactors can be positioned vertically or horizontally and can also assume positions between horizontal and vertical. Preferred for use as pyrolysis reactors are vertical tubular reactors whose inside tube diameters are approximately 10 to 100 mm and which have a tube length of approximately 0.5 to 5 m.

In accordance with the process of the invention, the cleavage of urethane is performed in the presence of thermally stable reactor packing. All inert, temperature-resistant, gas-permeable materials are suitable as packing. Examples are beads, wool, rings, or chips of carbon, steel, brass, copper, zinc, aluminum, titanium, chromium, cobalt, nickel, and quartz. Some of these materials, for example steel, brass, and zinc, have proven particularly successful and are, therefore, preferred.

The dissociation products are discharged from the reactor in the vapor phase. They are comprised almost exclusively of isocyanate and alcohol and are fed into a two-step vapor condensation unit. In the cleavage of 1,6-hexamethylenedibutylurethane shown in Example 1, a system pressure of from 20 to 40 mbar is used in the first condenser stage, using a condensation temperature of from 50° to 100° C., and in the second condensation stage a condensation temperature of −10° to 30° C. is used at the same system pressure.

As an alternative, especially when an additional solvent is used, the cleavage gases can be directed into one or more separating columns, whereby they are separated by means of distillation, in some cases using a substance with an intermediate boiling range. In a preferred embodiment, the intermediate-boiling-range substances are identical to the solvents cited above.

The resulting alcohol can be utilized without further purification to prepare, for example, urethanes. Thus a closed loop continuous cycle for the alcohol component is possible. The resulting isocyanate is generally distilled to improve purity, generally to a purity greater than 99.5 weight percent.

EXAMPLE 1

A piston-type metering pump with a heated pump head was used to inject 565 g of a mixture comprised of 80 weight percent 1,6-hexamethylene dibutylurethane and 20 weight percent decahydronaphthalene, within a period of 120 minutes, into a pyrolysis reactor constructed of V$_2$A steel, and having a length of 1000 mm and a diameter of 40 mm, which was packed with 3 mm V$_2$A wire mesh rings. The temperature of the nozzle was 170° C. Its spray pressure ranged from 150 to 160 bar. The pressure in the pyrolysis reactor was 14 mbar.

The gases resulting from pyrolysis were fractionally separated in a two-step condensation unit. A mixture of 76.5 weight percent 1,6-hexamethylenediisocyanate, 5.9 weight percent 6-butoxycarbonylaminohexylisocyanate, 1.7 weight percent unreacted 1,6-hexamethylene dibutylurethane, and 15.7 weight percent decahydronaphthalene was obtained in the first condensation step, which was operated at from 55° to 60° C. In the second condensation unit, operated at −5° C., 284 g of a mixture of butanol and decahydronaphthalene was collected. This mixture still contained 8.6 weight percent 1,6-hexamethylene dibutylurethane. From this, the conversion of 1,6-hexamethylene dibutylurethane was 93.6 percent, and the 1,6-hexamethylenediisocyanate yield was also 93.6 weight percent based on the reacted 1,6-hexamethylene dibutylurethane.

EXAMPLE 2

In a manner analogous to that used in Example 1, 550 g of a mixture comprised of 70 weight percent 1,6-hexamethylene dibutylurethane and 30 weight percent of a gasoline fraction having a boiling range between 155° and 180° C. was injected over a period of 120 minutes into a pyrolysis reactor heated to 420° C., packed with 3 mm V₂A wire mesh rings. The temperature of the nozzle was 200° C. The injection pressure was between 200 and 230 bar. The pressure in the pyrolysis reactor was 17 mbar.

The off-gases were fractionally separated in a two-step condensation unit. 245 g of a mixture comprised of 71.7 weight percent 1,6-hexamethylenediisocyanate, 9 weight percent 6-butoxycarbonylaminohexylisocyanate, 1.5 weight percent 1,6-hexamethylene dibutylurethane, and 18.4 weight percent gasoline was obtained in the first condensation stage, which was operated at from 55° to 60° C. In the second condensation unit, which was operated at −7° C., 278 g of a mixture comprised of butanol and gasoline was obtained. This mixture also contained 8.7 weight percent 1,6-hexamethylene dibutylurethane. The conversion of 1,6-hexamethylene dibutylurethane was 92.7 percent; the 1,6-hexamethylenediisocyanate yield was 91.9 percent based on reacted 1,6-hexamethylene dibutylurethane.

EXAMPLES 3-5

The method of Example 1 was used. The urethanes listed in the Table below were broken down into isocyanates as shown.

(b) pyrolyzing the urethane by injecting the urethane into a reduced pressure pyrolysis zone maintained at a temperature of from 175° C. to 600° C.; and
(c) recovering isocyanate and alcohol cleavage products thus produced.

2. The process of claim 1 wherein the urethane is heated in the liquid phase under pressure to temperatures of from 100° C. to 400° C.

3. The process of claim 1 wherein injecting the urethane into the pyrolysis zone is accomplished by means of a nozzle operating at elevated pressure.

4. The process of claim 3 wherein the nozzle has a spraying pressure of from 20 to 300 bar.

5. The process of claim 1 wherein pyrolysis of the urethane occurs at a temperature of from about 300° C. to about 480° C.

6. The process of claim 5 wherein pyrolysis of the urethane occurs at a pressure of from 0.1 to 200 mbar.

7. The process of claim 1 wherein the pressure of the pyrolysis zone is less than about 500 mbar.

8. The process of claim 1 wherein the pressure of the pyrolysis zone is from about 1 to about 100 mbar.

9. The process of claim 1 wherein the pyrolysis zone is filled with inert packing material.

10. The process of claim 1 wherein the urethane is mixed with an inert solvent.

11. The process of claim 10 wherein the urethane is mixed with the inert solvent in a urethane:solvent ratio of from about 100:5 to about 100:50 parts by weight.

12. The process of claim 10 wherein the boiling point of the inert solvent lies between the boiling points of the isocyanate and the alcohol.

TABLE

| Example | Urethane | Temp. (°C.) | Nozzle Injection Pressure (bar) | Thermolysis Temperature (°C.) | Isocyanate | Urethane Conversion (%) | Isocyanate Yield (%) |
|---|---|---|---|---|---|---|---|
| 3 | C₄H₉OCNH—(CH₂)₃—CH(CH₃)—CH₂—NHCOC₄H₉ (with C=O groups) | 180–200 | 220–230 | 415 | O=C=N—(CH₂)₃—CH(CH₃)—CH₂N=C=O | 88.7 | 94.2 |
| 4 | C₆H₄—NHCOCH₃ (with C=O) | 200–210 | 110–120 | 410 | C₆H₄—N=C=O | 37 | 97.6 |
| 5 | H₃C—C₆H₃(NHCOC₂H₅)(HN—COC₂H₅) | 130–140 | 200–230 | 390 | H₃C—C₆H₃(N=C=O)(N=C=O) | 98.3 | 88.1 |

The embodiments of the invention in which an exclusive privilege or property is claimed are defined as follows:

1. In a process for the vapor phase pyrolysis of urethanes to isocyanates in the absence of a catalyst, the improvement which comprises:
   (a) heating a urethane in the liquid phase under pressure;

13. The process of claim 1 wherein the urethane has the general formula:

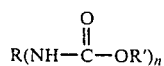

wherein R is a heterocyclic, aliphatic, cycloaliphatic, aromatic aliphatic, or aromatic radical having from 1 to 60 carbon atoms; and wherein R' is an aliphatic, aromatic, or aromatic-aliphatic radical having from 1 to 20 carbon atoms or a cycloaliphatic radical having from 3 to 15 carbon atoms, and wherein n is a whole number of from 1 to about 6.

14. The process of claim 1 wherein the isocyanate and alcohol cleavage products are separated by means of fractional condensation.

15. The process of claim 10 wherein the isocyanate and alcohol cleavage products are separated by means of fractional condensation.

16. The process of claim 12 wherein the isocyanate and alcohol cleavage products are separated by means of fractional condensation.

17. In a process for the vapor phase pyrolysis of urethanes to isocyanates in the absence of a catalyst, the improvement which comprises:
(a) heating a urethane in the liquid phase to a temperature of from 100° C. to 400° C. at a pressure of from 20 to 300 bar;
(b) pyrolyzing the urethane by injecting the urethane through a pressurized nozzle having an operating pressure of from 20 to 300 bar, into a pyrolysis zone maintained at a pressure less than 500 mbar and a temperature of from 175° C. to 600° C.; and
(c) recovering the isocyanate and alcohol cleavage products thus produced.

18. In a process for the vapor phase pyrolysis of urethanes to isocyanates in the absence of a catalyst, the improvement which comprises:
(a) heating a urethane in the liquid phase to a temperature of from 130° C. to 350° C. at a pressure of from 50 to 200 bar;
(b) pyrolyzing the urethane by injecting the urethane through a pressurized nozzle having an operating pressure of from 50 to 200 bar, into a pyrolysis zone maintained at a pressure of from 0.1 to 200 mbar and a temperature of from 300° C. to 480° C.; and
(c) recovering the isocyanate and alcohol cleavage products thus produced.

19. In a process for the vapor phase pyrolysis of urethanes to isocyanates in the absence of a catalyst, the improvement which comprises:
(a) heating a urethane in the liquid phase to a temperature of from 130° C. to 350° C. at a pressure of from 50 to 200 bar;
(b) pyrolyzing the urethane by injecting the urethane through a pressurized nozzle having an operating pressure of from 50 to 200 bar, into a pyrolysis zone maintained at a pressure of from 1 to 100 mbar and a temperature of from 360° C. to 440° C.; and
(c) recovering the isocyanate and alcohol cleavage products thus produced by means of fractional condensation.

20. The process of claim 19 wherein the urethane is dissolved in an inert solvent having a boiling point between the boiling points of the isocyanate and alcohol cleavage products.

* * * * *